United States Patent [19]
Davis

[11] Patent Number: 5,708,038
[45] Date of Patent: Jan. 13, 1998

[54] METHOD OF USING ALOE VERA AS A BIOLOGICAL VEHICLE

[75] Inventor: Robert H. Davis, King of Prussia, Pa.

[73] Assignee: Univera Pharmaceuticals, Inc., Broomfield, Colo.

[21] Appl. No.: 662,654

[22] Filed: Jun. 13, 1996

[51] Int. Cl.$^6$ .................................. A61K 47/42
[52] U.S. Cl. ........................................ 514/783
[58] Field of Search .................. 514/783; 424/195.1

[56] References Cited

U.S. PATENT DOCUMENTS 5,565,199  10/1996  Page et al. ........................ 424/195.1

OTHER PUBLICATIONS

Davis et al. (1991) JAPMA 81:1.
Elghamry and Shihata (1966) Plant Medica 14:352.
Fjösne et al. (1990) The Prostate 17:1.
Hart et al. (1988) J. of Ethnopharmacology 23:61–71.
Malini and Vanithakumari (1992) J. Ethnopharmacology 36:51.
Malini and Vanithakumari (1990) J. Ethnopharmacology 28:221.

Primary Examiner—Carlos Azpuru
Attorney, Agent, or Firm—Swanson & Bratschun L.L.C.

[57] ABSTRACT

The present invention provides a method for using Aloe vera as a biological vehicle for the delivery of drugs. In one embodiment Aloe vera is used as a biological vehicle to deliver the estrogen, β-estradiol and the androgen, testosterone propionate. The present invention also provides a method of treating symptoms and diseases mediated by hormonal deficiencies or amenable to treatment by hormones using Aloe vera as a biological vehicle.

34 Claims, 3 Drawing Sheets

METHOD OF USING ALOE VERA AS A BIOLOGICAL VEHICLE

FIELD OF INVENTION

The present invention relates generally to a method of using Aloe vera as a biological vehicle for the delivery of drugs. Specifically, this invention describes a method of using Aloe vera as a biological vehicle to deliver the estrogenic hormone, β-estradiol, and the androgenic hormone, testosterone. Further included in this invention is a method for treating hormonal deficiencies and conditions amenable to treatment with hormones using Aloe vera as a biological vehicle for delivery of the hormone.

BACKGROUND OF THE INVENTION

Aloe is an intricate plant which contains many biologically active substances. (Cohen et al. in *Wound Healing/Biochemical and Clinical Aspects*, 1st ed. WB Saunders, Philadelphia (1992)). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity, (See, e.g. Yagi et al. (1977) Z. Naturforsch 32c:731–734), and antioxidant activity (International Application Serial No. PCT/US95/07404).

Recent research has also shown that Aloe vera, a term used to describe the extract obtained from processing the entire leaf, isolated from the Aloe vera species of Aloe can be used as a vehicle for delivering the corticosteroid, hydrocortisone, administered both topically and subcutaneously, to the site of inflammation. (Davis et al. (1991) JAPMA 81:1). Davis et al. studied the topical and systemic anti-inflammatory activity of Aloe vera alone and in combination with hydrocortisone acetate. This study revealed that Aloe vera contributed in an additive way to the activity of the steroid, suggesting that Aloe vera may be useful as a biological vehicle for hydrocortisone. The significance of this finding is that if used in combination with Aloe vera, the dosage of the steroid can be reduced, while maintaining its biological activity, thereby reducing or eliminating any toxic side effects associated with higher dosages. These studies also revealed that Aloe vera assists in the penetration of hydrocortisone through the stratum corneum. Since Aloe vera contains many hydrophilic compounds, such as enzymes, amino acids and carbohydrates, as well as, hydrophobic compounds, such as vitamins and sterols, Davis et al. postulate that pharmacologic agents of both solubilities can be placed in Aloe vera and carried through the epidermal barrier. (Davis et al. (1991) JAPMA 81:1).

A vehicle is a substance, usually without biological activity, which is used as a medium for the administration of pharmacologic agents. Ideally a vehicle should be nonirritating and compatible with common medications. Criteria for vehicle selection include solubility of the active agent in the vehicle and the ability of the vehicle to penetrate physical barriers such as the stratum corneum and the lipid portion of the cell membrane. Consideration must also be given to any interactions between the vehicle and the active agent, the efficiency with which the vehicle releases the incorporated active ingredient, the molecular size and the composition of the vehicle. Traditional vehicles for subcutaneous administration include oils which tend to be irritating. Aloe vera has been shown to be nonirritating and nontoxic when injected subcutaneously in mice, even at massive doses.

Occasionally, a vehicle will have a synergistic effect, such that the final sum total of the activity in each system is greater than the sum of the components. As stated above, this is highly desirable in that less of the pharmacologic agent can be used to achieve the same effect, thereby reducing or eliminating any side effects associated with higher dosages.

The estrogens are a group of hormones which promote proliferation and growth of specific cells in the body and are responsible for the development and maintenance of secondary female sex characteristics. The estrogens are mainly responsible for cellular proliferation and growth of the tissues of the sexual organs and of other tissues related to reproduction. Estrogens also participate in the menstrual cycle. Naturally occurring estrogens, such as β-estradiol, estrone and estriol, are steroids produced primarily by the ovaries. β-Estradiol (referred to herein as estradiol) is involved in the maturation and cyclic function of accessory sex organs and the development of the duct system in mammary glands. Of the estrogen hormones, estradiol has the greatest physiological activity. When administered to ovariectomized mice, estrogens induce estrous and increase uterine weight. Studies have shown that microgram amounts of estradiol can increase the weight of the immature rat uterus in as few as six hours. (Astwood (1938) Anat. Rec. 70:25).

In hypogonadal women and menopausal women the level of estrogens in the blood decreases, causing a number of symptoms, including nervousness, depression, irritability and insomnia. There is also evidence that diminished estrogen levels contributes to a number of diseases, such as atherosclerosis and osteoporosis. Presently, estrogen replacement therapy is the only effective treatment for relief of the symptoms associated with decreased estrogen levels. Estrogens also have a protective effect against ischemic heart disease, (Martin et al. (1993) P.S.E.B.M. 202:288), tend to decrease the risk of coronary artery disease and have a favorable effect on plasma lipid and high density lipoproteins (antiatherogenic effect) in menopausal women. Currently, estrogen hormones are therapeutically used to treat any disorder attributable to estrogen deficiencies or any disorders amenable to estrogen therapy, such as various functional ovarian disorders, osteoporosis, certain coronary disorders in women, problems and discomforts associated with menopause, and certain types of cancer. Estrogens are also used in oral contraceptives.

Estrogens can be administered orally, by intramuscular or subcutaneous injection or by subcutaneous implantation. Astwood has established an estradiol response curve for mice of between 0.002 μg to 0.1 μg per day. The dose response curve for humans, as well as other animals, can be extrapolated from these results by taking into account the greater body weight of the person or animal under consideration.

Problems associated with estrogen therapy include; premenstrual tension, weight gain, fat deposition, fallopian tube blockage, increased risk of endometrial cancer and increased risk of gall bladder disease. The risk of endometrial cancer is dependant upon both the amount and duration of treatment, thus estrogens are typically administered at the lowest dose that will control symptoms.

Estrogens have been isolated from a number of plant sources, including willow wheat germ oil, date palm tree, clover and alfalfa. (Zarvow et al. (1961) Science 118:650). To date, no estrogens have been isolated from Aloe vera, however, three sterols having mild estrogenic activity: lupeol, campesterol and sitosterol have been isolated. Plant sterols can have a wide spectrum of biological activity, including mild estrogenic activity. (Malini and Vanithakumari (1990) J. Ethnopharmacology 28:221; Malini and Vanithakumari (1992) J. Ethnopharmacology 36:51). The estrogenic activity of plant sterols has been estimated to be approximately 1/400 of that recorded for estradiol. (Elghamry and Shihata (1966) Plant Medica 14:352).

Androgens, such as testosterone, are the male sex hormones, responsible for the development of male secondary sex characteristics. The androgenic hormones are steroids, secreted primarily by the testes. Androgens, specifically testosterone, are involved in the development and maintenance of secondary male sex characteristics, the maturation and normal function of accessory sex organs and are required for the maintenance of spermatogenesis. Additionally, androgens help to build muscle and cause nitrogen retention (anabolic), can also thicken bone and play a role in depositing calcium.

Androgen deficiencies, resulting from castration or inadequate gonadal function, referred to as hypogonadism, result in the regression or deficient development of secondary sexual characteristics. Androgen deficiencies are currently treated with various esters of testosterone, including testosterone propionate, administered by subcutaneous implantation or subcutaneous or intramuscular injection. Treatment with testosterone can restore testicular function, can maintain spermatogenesis and is important in testes repair. Studies have shown that castration causes atrophy and cellular changes in androgen dependent cells. This effect can be normalized by treatment with male hormones, specifically testosterone. (Fjösne et al. (1990) The Prostate 17:1). Androgens are also used to treat conditions in which there has been a tremendous loss of body weight and/or body protein, such as starvation or anorexia nervosa. Androgens may also improve male infertility.

Estrogens and androgens, such as β-estradiol or various esters of testosterone, are currently marketed dissolved in oil. However, oil has a number of shortcomings, for example, oil is allergenic and causes local intimation when injected intramuscularly or subcutaneously. Additionally, the absorption of oil is delayed long after the hormone is released. Vehicles for these compounds have, for the most part, been unsuitable.

SUMMARY OF THE INVENTION

The present invention includes a method of using Aloe vera as a biological vehicle for the delivery of pharmacologic agents. In one embodiment of the present invention, the method comprises administration of an estrogenic hormone, such as β-estradiol or androgenic hormone, such as testosterone, in combination with Aloe vera. The Aloe vera both increases the penetration of the drug through the stratum corneum and the cell membrane and contributes in an additive manner to the activity of each of the hormones.

The present invention also includes an improved method for the prevention and treatment of symptoms and diseases mediated by estrogen and androgen deficiencies or amenable to treatment with estrogen or androgen in patients suffering therefrom. This method comprises administration of a therapeutically effective amount of estrogen or androgen, respectively, in combination with Aloe vera.

It is to be understood that both the foregoing general description and the following detailed description are exemplary and explanatory only and are not restrictive of the invention as claimed.

DETAILED DESCRIPTION OF THE INVENTION

Figure 1:
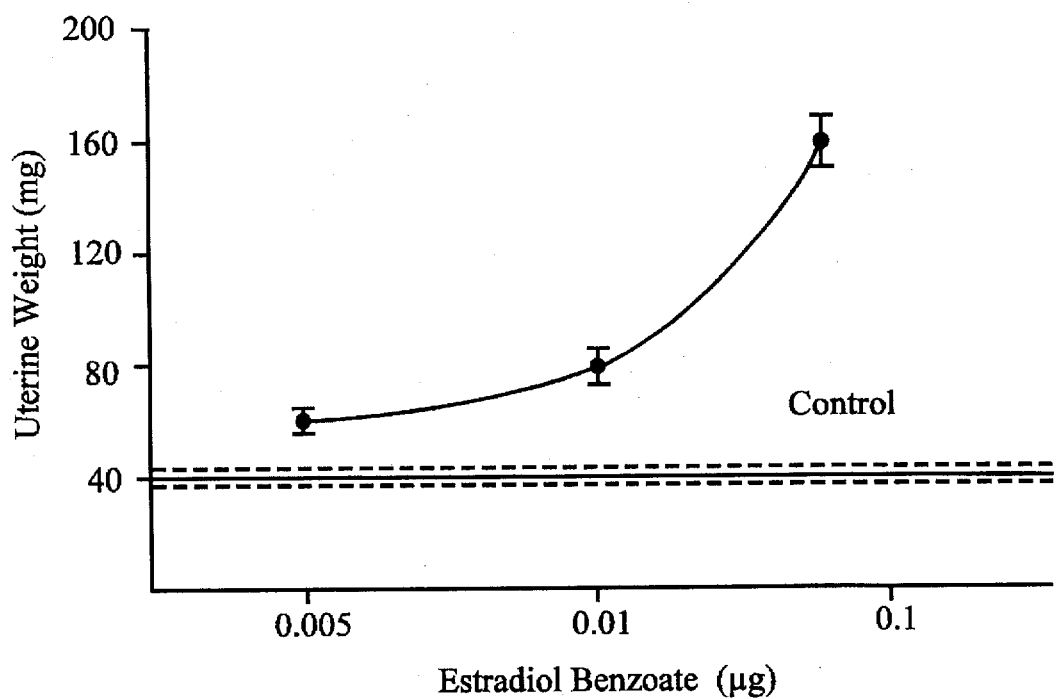
FIG. 1 depicts a dose response curve for estradiol benzoate in ovariectomized mice. The estradiol benzoate was administered subcutaneously over four days. The control group was subcutaneously administered the vehicle (corn oil) alone over four days.

The present invention includes a method of using Aloe vera, isolated from the Aloe plant, as a vehicle for the delivery of drugs. Specifically, this invention describes a method for using Aloe vera, as a biological vehicle to deliver estrogenic and androgenic hormones. In a preferred embodiment Aloe vera, isolated from the whole leaf of the *Aloe barbadensis* plant, is used as a biological vehicle to deliver the hormones estradiol benzoate and testosterone propionate. The method comprises the administration of a therapeutically effective amount of the hormone in combination with Aloe vera. While the primary goal of this invention is to provide methods for preventing and treating human diseases, the disclosure provided herein gives instruction of general physiological use, and veterinary uses are therefore also included within the scope of this invention.

The present invention further includes an improved method for preventing and treating symptoms and diseases mediated by estrogen and androgen deficiencies or any disorders amenable to estrogen or androgen therapy in patients suffering therefrom. This method comprises the administration of a therapeutically effective amount of an estrogen or androgen to a patient in need thereof in combination with Aloe vera.

Certain terms used to describe the invention herein are defined as follows:

The term "Aloe" refers to the genus of South African plants of the Liliaceae family of which the *Aloe barbadensis* plant is a species.

The term "Aloe vera" is defined as the dried juice of the whole leaf of various species of the Aloe plant. The "whole plant" Aloe vera used in the examples of this invention was prepared by "whole-leaf processing" of the whole leaf of the *Aloe barbadensis* plant. Briefly, whole leaves obtained from the *Aloe barbadensis* plant were ground, filtered, treated with cellulase (optional) and activated carbon and lyophilized. The lyophilized powder was reconstituted with water prior to use.

The term "estrogen" refers generically to estrus-producing steroid compounds, both naturally occurring and synthetic. Examples of estrogens include, but are not limited to, β-estradiol (referred to herein as "estradiol"), estrone and estriol. The term "estrogen" also refers to derivatives of these compounds which can be used in the treatment of symptoms or diseases mediated by estrogen deficiencies or amenable to treatment by estrogen. Some examples of derivatives are set forth below.

The term "androgen" refers generically to any substance that promotes masculization, both naturally occurring and synthetic. Examples of androgens include, but are not limited to methyltestosterone, testosterone, and derivatives thereof. Some examples of testosterone derivatives are set forth below.

A "vehicle" refers to a substance which acts as a physical or physiological carrier for active biological agents also referred to as pharmacologic agents. A vehicle aids in the penetration of pharmacologic agents through physical barriers, such as the stratum corneum and the lipid portion of cell membranes. A "biological vehicle" also adds biological activity to the pharmacologic agent regardless of the agent under consideration. In other words, a biological vehicle can have an additive or a synergistic effect as it enhances the effect of another pharmacologic agent.

A "symptom" or "disease" mediated by estrogen and androgen deficiencies or amenable to treatment by estrogens or androgens are well known to those in the art. A number of such symptoms and diseases are described above.

One embodiment of the present invention includes a method of using Aloe vera, as a biological vehicle for the delivery of drugs. Preferably, Aloe vera is used as a biological vehicle to deliver estrogen and androgen hormones, both naturally occurring and synthetic. Examples of estrogen hormones include, but are not limited to, β-estradiol, estrone and estriol or derivatives thereof. In a preferred embodiment the estrogenic hormone is an esterified derivative of β-estradiol selected from the group consisting of estradiol benzoate, estradiol cypionate, estradiol dipropionate, estradiol enanthate, estradiol ethynyl, estradiol undecylate, or estradiol valerate. Androgenic hormones include, but are not limited to methyltestosterone, testosterone and derivatives thereof. In a preferred embodiment the androgenic hormone is an esterified derivative of testosterone selected from the group consisting of testosterone cyclopentylpropionate (cipionate), testosterone enanthate (heptanoate), testosterone ethisterone (ethinyl), testosterone ketolaurate, testosterone phenylacetate, or testosterone propionate. In the most preferred embodiment Aloe vera, isolated from the whole leaf of the *Aloe barbadensis* plant, is used as a biological vehicle to deliver the hormones estradiol benzoate and testosterone propionate.

Example 1 demonstrates the effectiveness of Aloe vera as a biological vehicle for the delivery of estrogen. As discussed above, three sterols, lupeol, campesterol and sitosterol, known to have mild estrogenic activity, have been isolated from Aloe vera, therefore Aloe vera was first tested to determine whether it alone had any estrogenic activity. As can be seen in Table 1 (Example 1), whole leaf Aloe vera administered daily over a period of 7 days to ovariectomized mice at doses of 100 and 300 mg/kg per day per mouse did not induce estrous or increase uterine weight (Table 1). From this it can be concluded that Aloe vera, administered within this dose range does not have estrogenic activity, despite the fact that, as discussed above, it contains three sterols known to have mild estrogenic activity.

FIG. 1 (Example 1) depicts a dose response curve for the estrogenic hormone β-estradiol benzoate. In this example, the increase in uterine weight resulting from administration of estradiol benzoate to ovariectomized mice over a dose range of 0.005 µg to 0.1 µg was measured. As can be seen in FIG. 1, the average uterine weight of the ovariectomized mice administered estradiol benzoate subcutaneously for 4 days at a dosage of 0.005 µg was 69.2±1.5 mg and 177.7±7.8 mg at the higher 0.1 µg dose. The average uterine weight of the control group was 40 mg. The dose-response curve for estradiol benzoate, measuring increasing uterine weight, is very sensitive at small doses and has a long slope which can be continuously repeated. The variation recorded for the regression line is very small. Doses as small as $1/1000$ of a microgram can be assayed on the dose-response curve (FIG. 1).

Figure 2:
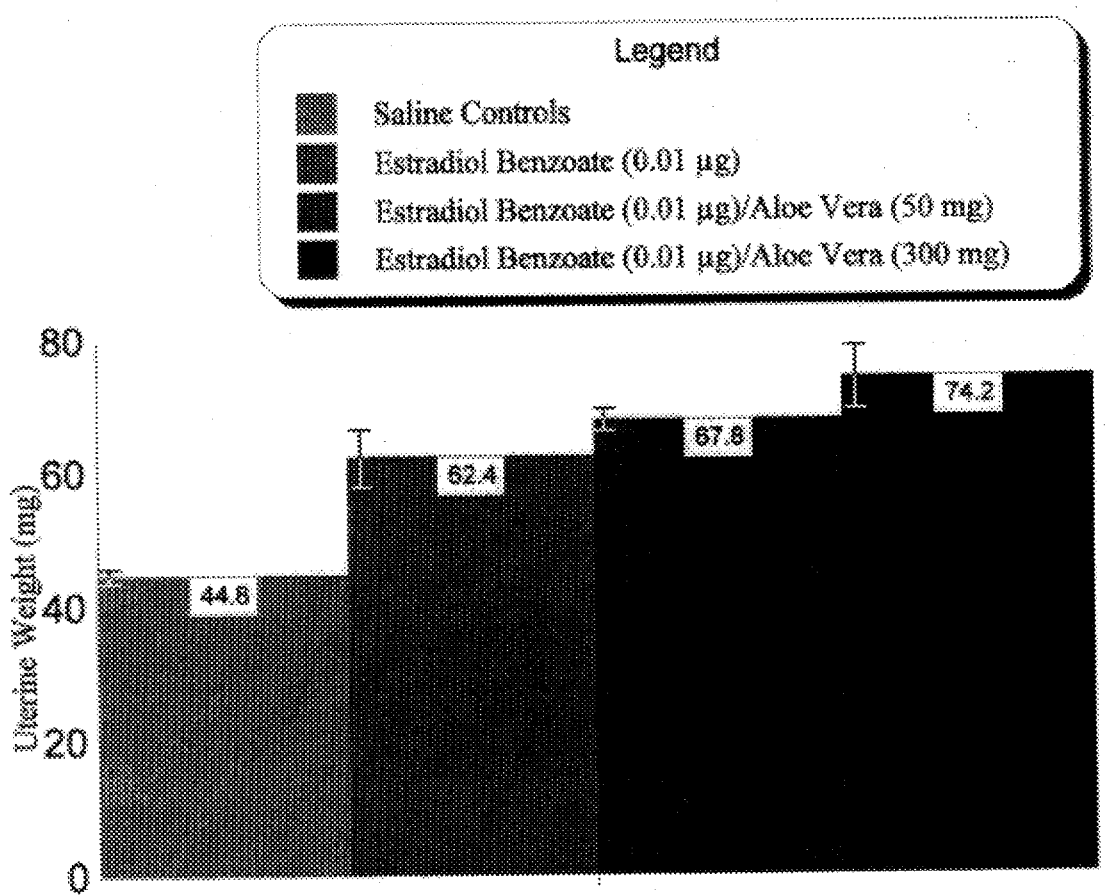
FIG. 2 depicts graphically the combined effect of Aloe vera and estradiol benzoate on uterine size in ovariectomized mice. The Aloe vera and estradiol benzoate were administered subcutaneously over five days. Each column represents the mean and standard error (S.E.) values for seven animals.

Referring to Table 2 and FIG. 2, it can be seen that when whole leaf Aloe vera is administered to ovariectomized mice, in combination with, estradiol benzoate, over a 5 day period the uterotropic effect of estradiol benzoate is significantly increased. As can be seen in Table 2, the saline injected ovariectomized mice, which was the control group, had a uterine weight of 44.8±0.7 mg. This weight was increased to 62.4±2.6 mg (a 39.3±1.6% increase over the controls) by administration of 0.01 µg estradiol benzoate. When the 0.01 µg estradiol benzoate was administered in combination with 50 mg/kg Aloe vera, the uterine weights increased to 67.8±1.3 mg (a 51.3±1.0% increase over controls). When 0.01 µg estradiol benzoate was given with 300 mg/kg of Aloe vera, uterine weights increased to 74.2±3.7 mg. This represents a 65.6% increase in uterine weight over controls. In fact, Aloe vera virtually doubled the uterotropic effect seen with estradiol benzoate alone. Thus, although Aloe vera has no estrogenic activity at these doses, it significantly increases the estrogenic response.

Figure 3:
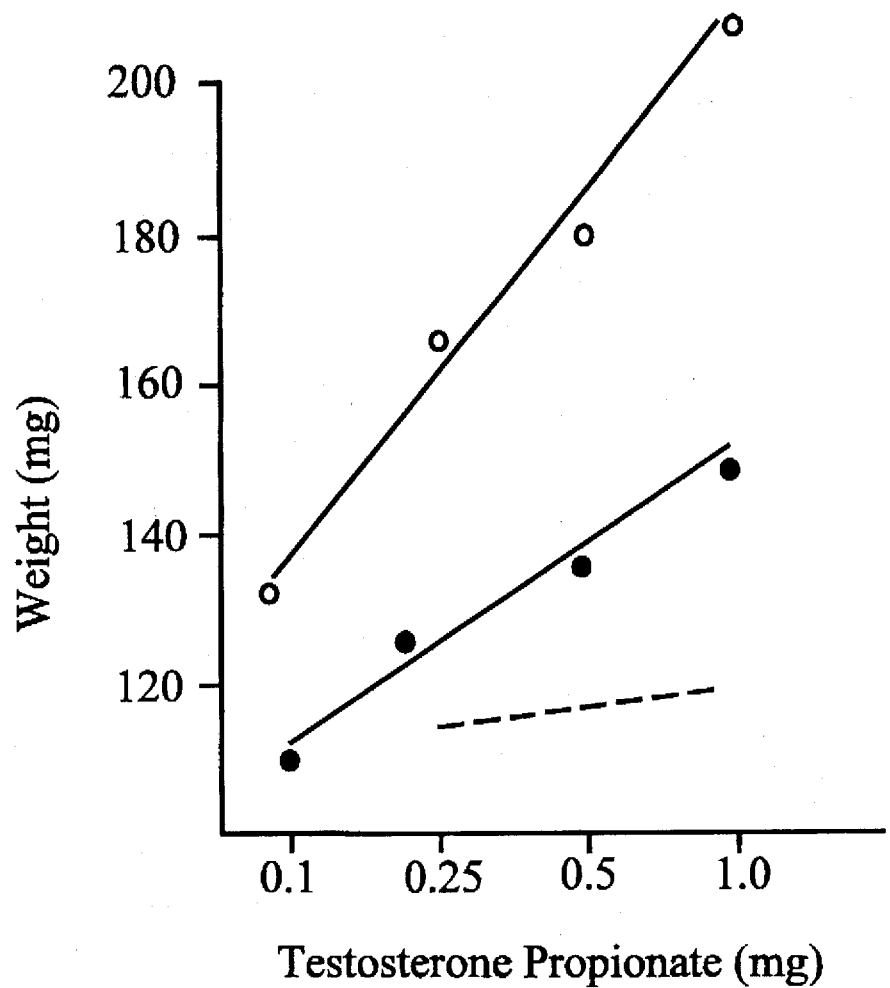
FIG. 3 depicts a dose response curve for testosterone propionate in immature castrated rats. The testosterone propionate was administered subcutaneously over seven days. The control group was subcutaneously administered vehicle (corn oil) alone over seven days. The graph depicts the increase in weight of the seminal vesicle (o) (control group–average weight=23 mg), ventral prostate (•) (control group–average weight=45 mg) and levator ani muscle (—) (control group–average weight=approximately 15 mg).

Example 2, demonstrates the effectiveness of Aloe vera as a vehicle for delivery of the androgenic hormone testosterone propionate. A dose response curve for testosterone propionate was first prepared using immature castrate rats. (FIG. 3). Immature castrate rats, rather than mice, were chosen because it is reported that rats provide the best models. (Dorfman et al. (1956) *Androgens*, John Wiley, London). The dose response curve was prepared by measuring the effect of testosterone propionate on the weight of the seminal vesicle, ventral prostate and the levator ani muscle, when administered to the rats over a dosage range of 0.1 to 1.0 mg per animal per day for 7 days. As can be seen in FIG. 3, the seminal vesicle weight (o) ranged from 132 mg to greater than 200 mg over the testosterone dose range of 0.1 mg to 1.0 mg per animal (control weight 23 mg). The ventral prostate (•) and levator ani muscle (—) were much less sensitive to administration of testosterone propionate.

Referring to Table 3, it can be seen that whole leaf Aloe vera administered to immature castrate mice, in combination with, testosterone propionate over a 4 day period significantly increased the effect of testosterone propionate on seminal vesicle weight. The dosage of testosterone propionate administered (25 µg) was determined from the dose response curve prepared using the castrate rats. Immature castrate mice, rather than rats, were used because mice are known to be somewhat more sensitive to Aloe vera and possibly to testosterone propionate. As can be seen in Table 3, the average weight of the seminal vesicle of mice receiving saline (control), corn oil (control) and Aloe vera (control) was 6.7 mg, 7.9 mg and 7.2 mg, respectively. The weight of the seminal vesicle was increased to an average of 20.9 mg by administration of testosterone propionate (25 µg) alone. This represents a 312±12% (A) increase in weight over the corn oil controls. When testosterone propionate (25 µg) was administered in combination with Aloe vera at a dosage of 150 mg/kg, the average weight of the seminal vesicle increased to 30.7 mg, a 461.0±28.5% (C) increase in weight over the corn oil controls. Aloe vera, alone, given at 150 mg/kg per day for 4 days gave an 8.1±0.9% (B) increase in seminal vesicle weight over the corn oil controls. Thus, the combined treatment with Aloe vera and testosterone propionate (C) has a greater effect on seminal vesicle weight than the additive effect of testosterone propionate (A) and Aloe vera (B) administered separately. In other words, A+B<C. Therefore, Aloe vera which has little androgenic activity has a synergistic relationship with testosterone propionate (Table 3).

The significance of these findings, as stated above, is that if Aloe vera is administered in combination with estrogens or androgens, lower doses of the hormones can be used to achieve the same therapeutic effect, thereby eliminating or reducing any side effects associated with higher doses. Additionally, Aloe vera is nontoxic and nonirritating, even at very large doses.

The method of treatment according to this invention comprises administering internally or topically to a subject in need of treatment an effective amount of an estrogenic or androgenic hormone dissolved in Aloe vera. In a preferred embodiment the Aloe vera is obtained by whole leaf processing, as discussed above. The estrogenic and androgenic hormones currently available for treatment are known to persons skilled in the art. Examples of estrogenic hormones include, but are not limited to, estradiol, estrone, estriol, and derivatives thereof. In one embodiment the estrogenic hormone is an esterified derivative of estradiol, selected from the group consisting of estradiol benzoate, estradiol cypionate, estradiol dipropionate, estradiol enanthate, estradiol ethynyl, estradiol undecylate, or estradiol valerate. In a preferred embodiment the estrogenic hormone is estradiol benzoate. Androgenic hormones include, but are not limited to, testosterone, methyltestosterone, and derivatives thereof. In a preferred embodiment the androgenic hormone is an esterified derivative of testosterone selected from the group consisting of testosterone cyclopentylpropionate (cipionate), testosterone enanthate (heptanoate), testosterone ethisterone (ethinyl), testosterone ketolaurate, testosterone phenylacetate, or testosterone propionate. In the most preferred embodiment the androgenic hormone is testosterone propionate.

The dose range for estrogens and androgens are well established and persons skilled in the art using routine clinical testing are able to determine optimum doses for the particular ailment being treated. It is anticipated that the doses of currently used hormones will decrease by an amount roughly corresponding to the percent increase in activity of the hormone due to the synergistic effect of Aloe vera. Currently estradiol is administered in a dose range of 1 to 2 mg per day for treatment of hypogonadal and menopausal women, 0.5 mg per day for treatment of osteoporosis, and 10 to 16 mg/kg of body weight per day for treatment of metastatic and/or progressive carcinoma.

Because estrogens have been reported to increase the risk of endometrial carcinoma, it is recommended that the lowest dose that will control symptoms be chosen.

Doses of estradiol benzoate hormone in the inventive method and pharmaceutical compositions containing the same are approximately 30 to 70% less than the current dose range when used in combination with 25 to 300 mg/kg (solid weight) of Aloe vera. Preferably the dose range is 40 to 60% less than the current dose range. This represents a decrease of up to 70% in the dose range currently used, which reflects the increase in the activity of the hormone due to the synergistic effect produced by Aloe vera.

The suggested dosage for androgens varies depending upon the age, gender and condition of the patient being treated. Replacement therapy in androgen-deficient males is currently between 10–50 mg of methyltestosterone daily. The current dosage of methyltestosterone for treatment of breast cancer is 50–200 mg per day. Testosterone propionate has a dose range of 20–100 mg/day.

Doses of testosterone propionate hormone in the inventive method and pharmaceutical compositions containing the same are up to approximately 70 to 80% less than the current dose range when used in combination with 25 to 300 mg/kg (solid weight) of Aloe vera. This represents a decrease of up to 80% in the dose range currently used, which reflects the increase in the activity of the hormone due to the synergistic effect produced by Aloe vera. The dose range of other hormones can be determined in a like manner.

Ailments that may be treated according to the method of the present invention include any disorder attributable to estrogen or androgen deficiencies or any disorders amenable to estrogen or androgen therapy. As discussed above estrogen therapy is currently used to treat various functional ovarian disorders, osteoporosis, certain coronary disorders in women, problems and discomforts associated with menopause, and certain types of cancer. Estrogens are also used in oral contraceptives. Androgen therapy is currently used to treat hypogonadism, certain types of cancer, and as an anabolic agent.

The therapeutic compositions of the present invention are preferably administered parenterally by injection, although other effective administration forms, such as intraarticular injection, inhalant mists, orally active formulations, transdermal iontophoresis or suppositories, are also envisioned. It is contemplated that other pharmaceutically acceptable solvents may be used together with Aloe vera. Such solvents are well known to those in the art. In one preferred embodiment it is envisioned that the Aloe vera and the hormone constitute a physiologically-compatible, slow-release formulation. In addition, the formulation may contain other pharmacologically-acceptable excipients for modifying or maintaining the pH, osmolarity, viscosity, clarity, color, sterility, stability, rate of dissolution, or odor of the formulation. Similarly, the formulation may contain still other pharmacologically-acceptable excipients for modifying or maintaining the stability, rate of dissolution, release, or absorption of the hormone and Aloe vera. Such excipients are those substances usually and customarily employed to formulate dosages for parenteral administration in either unit dose or multi-dose form.

Preferably, the manner of administering the formulations containing the Aloe vera/hormone mixture for systemic delivery is via subcutaneous, intramuscular, intravenous, intranasal or vaginal or rectal suppository. Preferably the manner of administration of the formulations for local delivery is via intraarticular, intratracheal, or instillation or inhalations to the respiratory tract.

It is also contemplated that certain formulations containing Aloe vera/hormone are to be administered orally. Preferably, formulations administered in this fashion are encapsulated. The encapsulated Aloe vera/hormone may be formulated with or without those carriers customarily used in the compounding of solid dosage forms. Preferably, the capsule is designed so that the active portion of the formulation is released at that point in the gastro-intestinal tract when bioavailability is maximized and pre-systemic degradation is minimized. Additional excipients may be included to facilitate absorption of the active ingredients. Diluents, flavorings, low melting point waxes, vegetable oils, lubricants, suspending agents, tablet disintegrating agents, and binders may also be employed.

Regardless of the manner of administration, the specific dose is calculated according to the approximate body weight of the patient. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

It should be noted that the invention described herein may be used for veterinary as well as human applications and that the term "patient" should not be construed in a limiting manner. In the case of veterinary applications, the dosage ranges can be determined as described above, taking into account the body weight of the animal.

It is understood that the application of teachings of the present invention to a specific problem or environment will be within the capabilities of one having ordinary skill in the art in light of the teachings contained herein. Examples of representative uses of the present invention appear in the following examples.

The following examples describe the application of the present invention to administration of the estrogen hormone, estradiol and the androgen hormone, testosterone. The examples are provided for illustrative purposes only and are not intended to limit the scope of the invention. It is contemplated that Aloe vera will act as a biological vehicle for the delivery of any compounds containing aromatic rings. There are many important pharmacologic agents which fall into this category.

EXAMPLES

Materials. The whole plant Aloe vera used in the following examples was supplied by Aloecorp (Irving, Tex.), in the form of the lyophilizate. The lyophilizate was prepared by "whole-leaf processing" of the leaves of the *Aloe barbadensis* plant. Briefly, whole leaves were ground and filtered to yield a green viscous gel, treated with cellulase and then treated with activated carbon prior to lyophilization. The lyophilizate was reconstituted with water prior to injection. Estradiol benzoate and testosterone propionate were purchased from Sigma Chemical Company (St. Louis, Mo.).

Example 1. Demonstration of Aloe Vera as a Biological Vehicle for Estrogen

Adult female mice weighing approximately 30 g (10 animals/group; HSD-ICR; Frederick Maryland Colony) were used in this study. The whole plant Aloe vera was prepared as described above. The mice were ovariectomized and five days later treated as described below.

Measurement of Estrogenic Activity of Whole Leaf Aloe Vera

To determine whether whole leaf Aloe vera has any estrogenic activity the animals were treated as follows: Group I: ovariectomized animals treated with saline (carrier) alone 10 mL/kg per day per mouse injected subcutaneously for 7 days; Group II: ovariectomized animals treated with 100 mg/kg (solid weight) of whole plant Aloe vera per day per mouse injected subcutaneously for 7 days; Group III: ovariectomized animals treated with 300 mg/kg of whole plant Aloe vera per mouse per day for 7 days. On day 12, each animal was vaginally smeared to determine the stage of the estrous cycle each of the mice were in. The uterus was removed from each animal, blotted dry on filter paper and weighed. The standard error for each mean was recorded. The data is recorded in Table 1. As can be seen in Table 1, at the doses used in this study Aloe vera has no estrogenic activity, as measured by vaginal smear and increase in uterine weight.

Dose-Response Curve for Estradiol Benzoate

To obtain a dose-response curve for estradiol benzoate in ovariectomized mice, the mice were treated as follows: Group IV: ovariectomized animals treated with carrier (corn oil) alone, 0.1 mL per day per mouse injected subcutaneously for 4 days; Group V: ovariectomized animals treated with 0.005 µg estradiol benzoate per mouse per day injected subcutaneously for 4 days; Group VI: ovariectomized animals treated with 0.01 µg estradiol benzoate per mouse per day injected subcutaneously for 4 days; Group VII: ovariectomized animals treated with 0.1 µg estradiol benzoate per mouse per day injected subcutaneously for 4 days. On day 5, the uterus from each animal was removed, blotted and weighed. The results are depicted in FIG. 1. As can be seen in FIG. 1, the average uterine weight of the ovariectomized mice administered estradiol benzoate subcutaneously for 4 days at a dosage of 0.005 µg increases from 40 mg (control) to 69.2±1.5 mg and to 177.7±7.8 mg at the higher 0.1 µg dose.

Measure of Estrogenic Activity of the Combination of Estradiol Benzoate and Whole Leaf Aloe Vera To determine the estrogenic activity for treatment with a combination of estradiol benzoate and whole plant Aloe vera the animals were treated as follows: Group VIII: ovariectomized animals were treated with saline (controls), 10 mL/kg per day per mouse administered subcutaneously for 4 days; Group IX: ovariectomized animals treated with 0.01 µg estradiol benzoate in corn oil (0.1 mL) per animal per day administered subcutaneously for 4 days; Group X: ovariectomized animals treated with 0.01 µg estradiol benzoate and 50 mg/kg whole leaf Aloe vera administered subcutaneously per mouse per day for 4 days; and Group XI: ovariectomized animals treated with 0.01 µg estradiol benzoate and 300 mg/kg whole leaf Aloe vera administered subcutaneously per mouse per day for 4 days. On day 5, the uterus from each mouse was removed, blotted and weighed. The whole leaf Aloe vera and estradiol were administered separately over the 4 day daily injection period. The results are set forth in Table 2.

Example 2. Demonstration of Aloe Vera as a Biological Vehicle for Testosterone

The immature castrate mice used in this study weighed approximately 15 g (10 animals/group; HSD-ICR; Frederick Maryland Colony). The whole plant Aloe vera was prepared as described above.

Dose-Response Curve for Testosterone Propionate

To obtain a dose-response curve for testosterone propionate the animals were treated as follows: Group I: immature castrate rats were treated with vehicle (corn oil) alone, 0.1 mL per day per mouse injected subcutaneously for 7 days; Group II: immature castrate rats were treated with 0.1 mg of testosterone propionate per day per rat injected subcutaneously for 7 days; Group III: immature castrate rats were treated with 0.25 mg of testosterone propionate per day per rat injected subcutaneously for 7 days; Group IV: immature castrate rats were treated with 0.5 mg of testosterone propionate per day per rat injected subcutaneously for 7 days; Group V: immature castrate rats were treated with 1.0 mg of testosterone propionate per day per rat injected subcutaneously for 7 days. On day 8, the seminal vesicle, ventral prostate and levator ani muscle was removed from each animal and weighed. The results are depicted in FIG. 3.

Measure of Androgenic Activity of the Combination of Testosterone Propionate and Whole Leaf Aloe Vera To determine the androgenic activity of testosterone propionate resulting from treatment with a combination of testosterone propionate and whole plant Aloe vera the animals were treated as follows: Group I: immature castrate mice were treated with saline (controls), 10 mL/kg per day per mouse administered subcutaneously for 4 days; Group II: immature castrate mice were treated with corn oil (controls), 0.1 mL per day per mouse administered subcutaneously for 4 days; Group III: immature castrate mice were treated with Aloe vera, 150 mg/kg per day per mouse administered subcutaneously for 4 days; Group IV: immature castrate mice were treated with 25 µg of testosterone propionate in corn oil per animal per day administered subcutaneously for four days; Group V: immature castrate mice were treated with treated with 25 µg of testosterone propionate in corn oil and 150 mg/kg Aloe vera per animal per day administered subcutaneously for 4 days. On day 5, the seminal vesicle from each mouse was removed, blotted and weighed. The whole leaf Aloe vera and testosterone were administered separately over the 4 day daily injection period. The results are set forth in Table 3.

TABLE 1

EFFECT OF ALOE VERA ON OVARIECTOMIZED MICE

| Aloe vera Treatment[1] mg/kg | Number of Mice in Estrous | Uterine Weight (mg) |
| --- | --- | --- |
| Saline Controls | 1/10 | 27.2 ± 2.6 |
| 100 | 0/9 | 29.0 ± 4.1[2] |
| 300 | 0/11 | 29.0 ± 2.0[2] |

[1]Administered subcutaneously (7 days); 10 animals per group
[2]P > 0.5 ± standard error (S.E.)

TABLE 2

EFFECT OF ALOE VERA/ESTRADIOL BENZOATE ON OVARIECTOMIZED MICE

| TREATMENT[1] | UTERINE WEIGHT | |
| --- | --- | --- |
|  | mg | Percent Increase |
| Saline Controls | 44.8 ± 0.7 | — |
| Estradiol Benzoate (0.01 µg) | 62.4 ± 2.6 | 39.3 ± 1.6 |
| Estradiol Benzoate (0.01 µg) Aloe Vera (50 mg/kg) | 67.8 ± 1.3 | 51.3 ± 1.0 |
| Estradiol Benzoate (0.01 µg) Aloe Vera (300 mg/kg) | 74.2 ± 3.7 | 65.6 ± 3.3 |

[1]Administered subcutaneously (5 days); 10 animals/group

TABLE 3

EFFECT OF ALOE VERA ON THE STIMULATION OF THE SEMINAL VESICLES OF IMMATURE CASTRATE MALE MICE

| Treatment* | Seminal Vesicle | |
| --- | --- | --- |
|  | Weight (mg) | % Increase |
| Saline Control | 6.7 ± 0.6 | — |
| Corn Oil Control | 7.9 ± 0.7 | 18.0 ± 1.6 |
| Testosterone Propionate (25 µg) | 20.9 ± 0.8 | 312.3 ± 12.0 (A) |
| Testosterone Propionate (25 µg) Aloe vera (150 mg/kg) | 30.7 ± 1.9 | 461.0 ± 28.5 (C) |
| Aloe vera (150 mg/kg) | 7.2 ± 0.8 | 8.1 ± 0.9 (B) |

*Administered subcutaneously each day for 4 days; 10 animals/group.

What is claimed is:

1. A method of using Aloe vera as a vehicle for the delivery of estrogenic hormones comprising administration of the estrogenic hormone in combination with Aloe vera.

2. The method of claim 1 wherein the Aloe vera is derived from the *Aloe barbadensis* plant.

3. The method of claim 1 wherein the estrogenic hormone is selected from the group consisting of β-estradiol, estrone, estriol, or derivatives thereof.

4. The method of claim 3 wherein the estrogenic hormone is an esterified derivative of β-estradiol.

5. The method of claim 4 wherein the esterified derivative of β-estradiol is selected from the group consisting of estradiol benzoate, estradiol cypionate, estradiol dipropionate, estradiol enanthate, estradiol ethynyl, estradiol undecylate, or estradiol valerate.

6. A method of using Aloe vera as a vehicle for the delivery of androgenic hormones comprising administration of the androgenic hormone in combination with Aloe vera.

7. The method of claim 6 wherein the Aloe vera is derived from the *Aloe barbadensis* plant.

8. The method of claim 6 wherein the androgenic hormone is selected from the group consisting of methyltestosterone, testosterone or derivatives thereof.

9. The method of claim 8 wherein the androgenic hormone is an esterified derivative of testosterone.

10. The method of claim 9 wherein the esterified derivative of testosterone is selected from the group consisting of testosterone cyclopentylpropionate (cipionate), testosterone enanthate (heptanoate), testosterone ethisterone (ethinyl), testosterone ketolaurate, testosterone phenylacetate or testosterone propionate.

11. A method for treating estrogenic deficiencies and conditions amenable to treatment by estrogens comprising administering to a patient in need thereof a therapeutically effective amount of an estrogenic hormone in combination with Aloe vera.

12. The method of claim 11 wherein the Aloe vera is derived from the *Aloe barbadensis* plant.

13. The method of claim 11 wherein the estrogenic hormone is selected from the group consisting of β-estradiol, estrone, estriol, or derivatives thereof.

14. The method of claim 13 wherein the estrogenic hormone is an esterified derivative of β-estradiol.

15. The method of claim 14 wherein the esterified derivative of β-estradiol is selected from the group consisting of estradiol benzoate, estradiol cypionate, estradiol dipropionate, estradiol enanthate, estradiol ethynyl, estradiol undecylate, or estradiol valerate.

16. The method of claim 11 wherein the condition amenable to treatment by estrogen hormones is selected from the group consisting of ovarian disorders, osteoporosis, coronary disorders, and problems associated with menopause or cancer.

17. A method for treating androgenic deficiencies and conditions amenable to treatment by androgens comprising administering to a patient in need thereof a therapeutically effective amount of an androgen hormone in combination with Aloe vera.

18. The method of claim 17 wherein the Aloe vera is derived from the *Aloe barbadensis* plant.

19. The method of claim 17 wherein the androgenic hormone is selected from the group consisting of methyltestosterone, testosterone or derivatives thereof.

20. The method of claim 18 wherein the androgenic hormone is an esterified derivative of testosterone.

21. The method of claim 20 wherein the esterified derivative of testosterone is selected from the group consisting of testosterone cyclopentylpropionate (cipionate), testosterone enanthate (heptanoate), testosterone ethisterone (ethinyl), testosterone ketolaurate, testosterone phenylacetate or testosterone propionate.

22. The method of claim 18 wherein the condition amenable to treatment by androgen hormones is selected from the group consisting of hypogonadism or cancer.

23. A method for treating conditions amenable to treatment by an estrogenic hormone comprising administering to a patient in need thereof an efficacious amount of a composition comprising an estrogen and Aloe vera.

24. The method of claim 23 wherein the amount of Aloe vera in the composition is between 25 and 300 mg/kg of body weight.

25. The method of claim 23 wherein the Aloe vera is derived from the *Aloe barbadensis* plant.

26. The method of claim 23 wherein the estrogenic hormone is selected from the group consisting of β-estradiol, estrone, estriol, or derivatives thereof.

27. The method of claim 23 wherein the estrogenic hormone is an esterified derivative of β-estradiol.

28. The method of claim 27 wherein the esterified derivative of β-estradiol is selected from the group consisting of estradiol benzoate, estradiol cypionate, estradiol dipropionate, estradiol enanthate, estradiol ethynyl, estradiol undecylate, or estradiol valerate.

29. A method for treating conditions amenable to treatment by an androgenic hormone comprising administering to a patient in need thereof an efficacious amount of a composition comprising an androgen and Aloe vera.

30. The method of claim 29 wherein the amount of Aloe vera in the composition is between 25 and 300 mg/kg.

31. The method of claim 29 wherein the Aloe vera is derived from the *Aloe barbadensis* plant.

32. The method of claim 29 wherein the androgenic hormone is selected from the group consisting of methyltestosterone, testosterone or derivatives thereof.

33. The method of claim 29 wherein the androgenic hormone is an esterified derivative of testosterone.

34. The method of claim 33 wherein the esterified derivative of testosterone is selected from the group consisting of testosterone cyclopentylpropionate (cipionate), testosterone enanthate (heptanoate), testosterone ethisterone (ethinyl), testosterone ketolaurate, testosterone phenylacetate or testosterone propionate.

* * * * *